United States Patent [19]
Eriksson

[11] Patent Number: 5,720,715
[45] Date of Patent: Feb. 24, 1998

[54] ANKLE BANDAGE

[75] Inventor: Thomas Eriksson, Tyreso, Sweden

[73] Assignee: Rehband Anatomiska AB, Sollentuna, Sweden

[21] Appl. No.: 590,230

[22] Filed: Jan. 23, 1996

[30] Foreign Application Priority Data

Feb. 22, 1995 [SE] Sweden ................................ 9500657

[51] Int. Cl.$^6$ .................................................... A61F 5/00
[52] U.S. Cl. ............................ 602/65; 602/23; 602/27; 602/62
[58] Field of Search ........................ 602/6, 7, 27, 65; 607/101, 23, 62

[56] References Cited

U.S. PATENT DOCUMENTS

| 216,106 | 6/1879 | Pugsley | 602/65 |
|---|---|---|---|
| 4,019,505 | 4/1977 | Wartman . | |
| 4,133,311 | 1/1979 | Karczewski | 602/65 |
| 4,600,618 | 7/1986 | Raychok, Jr. . | |
| 4,638,794 | 1/1987 | Grisar | 602/27 |
| 4,862,900 | 9/1989 | Hefele | 602/27 |
| 5,000,195 | 3/1991 | Neal . | |
| 5,038,762 | 8/1991 | Hess | 602/27 |
| 5,226,875 | 7/1993 | Johnson . | |
| 5,288,286 | 2/1994 | Davis . | |
| 5,415,624 | 5/1995 | Williams | 602/21 |
| 5,501,659 | 3/1996 | Morris et al. | 602/65 X |

FOREIGN PATENT DOCUMENTS

| 0 468 351 A1 | 1/1992 | European Pat. Off. . | |
| 499710 | 8/1992 | European Pat. Off. | 602/27 |

Primary Examiner—Richard J. Apley
Assistant Examiner—Denise Pothier
Attorney, Agent, or Firm—Townsend and Townsend and Crew LLP

[57] ABSTRACT

An ankle bandage (1) for supporting an ankle and foot while allowing a relatively unimpeded walk. The ankle bandage has a generally sock-shaped main body enclosing the ankle and instep region of a user. The main body may be opened at a front closure and is made from a flexible, resilient, heat insulating material. A pocket (8,9,10) for containing a stabilizing support body (11) is defined by a separate material sewn on the inside of main body along seams 6 and 7. The supporting body (11) comprises two rail portions (18) extending from a point above the ankle area of the user on each side of the leg, a joining portion (19) coupling the upper ends of the rail portions and a heel support formed by distal tapering portions of the lower ends (20) of the rail portions (18). During use, the tapering portions do not overlap and the heel support is located below the instep area and against the outside of the foot. The heel support has a narrow width compared to the upper ends of the rail portions (18) which allows a comfortable and normal pivoting ankle motion during walking while maintaining support.

18 Claims, 2 Drawing Sheets

ANKLE BANDAGE

BACKGROUND OF THE INVENTION

This invention relates generally to an ankle bandage. Specifically, the invention relates to an ankle bandage having a generally sock-shaped main body surrounding the ankle and heel region of a user. The main body includes various openings and is made from a flexible, resilient, heat insulating material. The main body further includes a pocket for containing a stabilizing element, also called a supporting body.

A typical bandage is shown in U.S. Pat. No. 5,000,195, wherein the stabilizing elements are U-shaped rails placed in U-shaped pockets. The pockets are located on each side of the bandage. The rails extend from the upper part of the bandage to a position below the ankles. However, this bandage is not capable of giving sufficient stability and control to the heel bone, even though a flexible but non-resilient band is intended to surround and wrap below the heel region. The reason for this is that the band allows undesired movement of the heel bone during walking due to the flexibility of the band. This particular arrangement of the rails, with each having a free end directed upwards, results in an unstable bandage that does not provide sufficient stability in the region of the ankle.

U.S. Pat. No. 5,226,875 concerns a shoe having a integral ankle support. A stabilizing element is wrapped under the heel region of the foot and extends up each side of the foot to an area above the ankles. The upwardly extending parts comprise two free ends and the portion under the heel has a considerable width in the longitudinal direction of the foot. The movability of the foot is reduced and the risk of abrasion sores occurs, particularly against middle foot bone V (Metatarsal V) on the outside of the foot.

The present invention eliminates the drawbacks of the prior art by providing an ankle bandage which gives full support for the ankle region and the heel bone. The ankle bandage according to the present invention also allows good movability of the foot in a vertical plane through the lower leg and the foot, so as to allow an unimpeded walk, while maintaining the desired support of the ankle and foot area.

SUMMARY OF THE INVENTION

According to the invention, an ankle bandage is composed of a main body with a rigid, stabilizing support body.

In a preferred embodiment, the main body is generally sock-shaped and surrounds the ankle, heel and instep region of the user. The main body is made from a flexible, resilient, heat insulating material and may be opened at a front closure. The main body also has a pocket sides designed to hold the supporting body along the medial and lateral sides of the main body. The supporting body is fitted to a user's foot, ankle and lower leg and is manufactured from a sheet of heat formable material. The supporting body comprises two rail portions each having upper and lower ends which are arranged in a longitudinal direction from an area above the ankle region of the user and extend down the respective medial and lateral sides of the main body to enclose the ankle. The rail portions are coupled by a joining portion at the upper ends of the rail portions. A heel support is formed by distal tapering portions of the lower ends of the rail portions. The heel support is located below the heel bone region of the user at the instep region of the foot. The heel support has a small width relative to both the length of the foot and the upper ends of the rail portions. A side of the heel support is located against the outside of the foot.

The stabilizing element is preferably a rigid support body made from a sheet of heat formable material. The resulting enclosing support structure has very good rigidity in the upper part of the bandage, stability for the ankle region and the desired support for the heel bone. By the portion of the supporting body under the foot having a small width, usually between about 0.7 to 1.8 cm wide, support is obtained at the same time as movement in a vertical plane is essentially unimpeded. The lower end of the rail portion against the outer portion of the foot, which also has a small width, prevents abrasive injuries, particularly against middle foot bone V (Metatarsal V), which is located at the outside of the foot.

The integral, inverse U-shaped supporting body provides a simple ankle bandage and easy production while maintaining stability. The resulting shape, which is designed to avoid affecting the Achilles' tendon, provides both support and comfort during use.

The joining portion of the supporting body may be arranged at the posterior side of the leg. This provides particularly good comfort for the user.

The supporting body is preferably a thermoplastic material and heat formable at a temperature above the body temperature of the user. This allows for an easy adjustment to a particular patient and a perfect fit for the individual user. When a patient has ceased to use the bandage, it may be adjusted to and used by the next patient after reheating.

The supporting body preferably absorbs and is heated by microwaves. This allows the supporting body to be heated up to its plastic temperature when it is enclosed inside the main body without need for hot water baths or the like.

Preferably the supporting body is comprised of a thermoplastic material, such as a bandage material sold under the trademark Turbocast (reg. trademark). This type of material ensures that the supporting body has rigid properties at the temperature of use and the plastic properties at a reasonably heated state.

The sheet of material for the supporting body can be perforated with a number of holes. This facilitates the transport of body moisture from the user's foot to an outer portion of the bandage during use.

The pocket in the main body is preferably formed between two layers of flexible, resilient heat insulating material. This configuration of the pocket provides comfort and reduced abrasion to the foot. In addition, during initial fitting to the user, the supporting body maintains its heated, plastic state at a sufficiently high temperature a sufficiently long period of time to allow appropriate adjustment.

The use of a front closure for the main body allows for a simple attachment of the bandage onto the ankle and foot of a patient.

The distal tapering portions of the lower ends of the rail portions do not overlap below foot. This reduces the thickness of the bandage below the foot and enhances comfort.

These and other features and advantages of the present invention will be more fully understood from the following detailed description which should be read in light of the accompanying drawings.

DESCRIPTION OF SPECIFIC EMBODIMENTS

Figure 1:
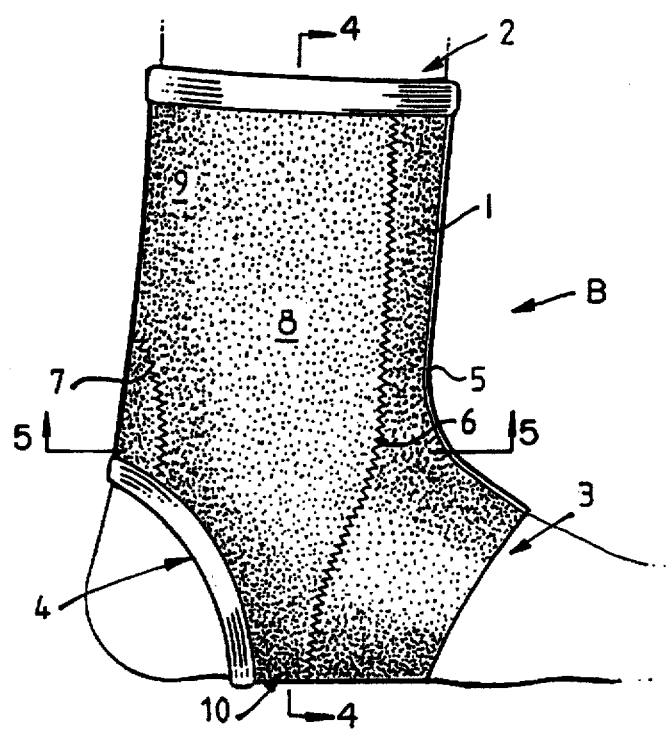
FIG. 1 shows in a side view an ankle bandage according to the invention applied onto the foot of a patient.

The ankle bandage B shown in FIG. 1 includes a main body 1 which extends from a point 2 above the ankle area downwards in a sock-shaped manner and surrounds the instep region of the foot of the patient. An opening at 3 in front of a line through the front edge of the skin bone is intended for the front part of the foot and the end of the heel is also free through an opening defined by edge 4. The front side of the bandage may be opened at 5 so as to allow comfortable attachment by the patient. The ankle bandage B is wrapped from the back of the leg and from below the foot and is subsequently closed by fasteners, such as Velcro® brand hook and loop fasteners at 5.

The main body 1 comprises a front seam 6 along each side, which extends in an essentially vertical direction on the sock-shaped portion of the ankle bandage and obliquely backwards in a curved manner towards the heel portion of the bandage, such that the seam 6 (at least at the outside of the foot) passes well behind Metatarsal V. Main body 1 also comprises an inverse U-shaped rear seam 7, which is located in the area of the Achilles' tendon. The combination of seams 6 and 7 and the edge of the opening at 4 define a pocket 25 for a supporting body 11 whereby the pocket is defined by an outside material layer 26 of the ankle bandage and a similar inside material layer 27 on an inner surface of the bandage, which is sewn to the outside material layer at seams 6, 7 and 4. The pocket has two main pocket areas 28, 29 for the rail portions 18 of the supporting body 11 (see FIG. 3), an area 9 for the joining portion 19 and areas 10 beneath the instep of the user's foot for the lower ends 20 of the supporting body 11.

Figure 2:
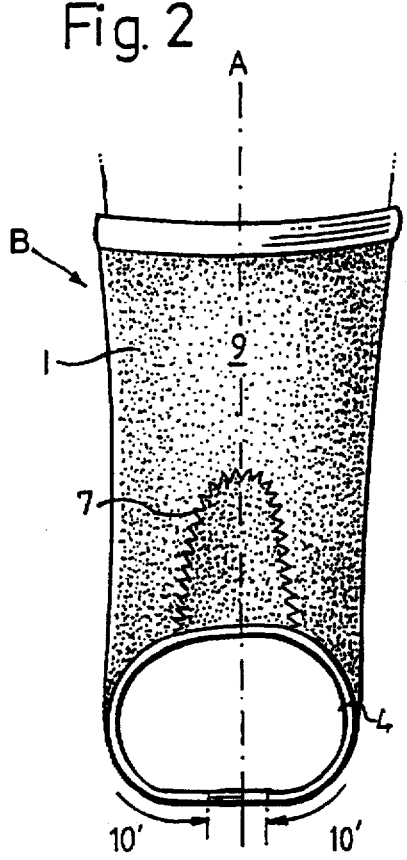
FIG. 2 shows the bandage according to FIG. 1 as seen from behind.
Figure 4:
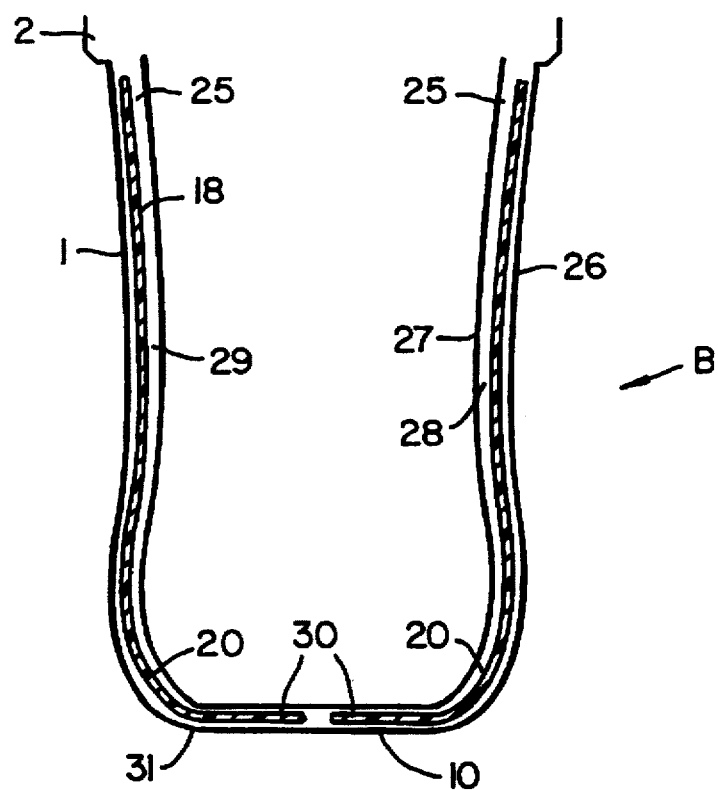
FIG. 4 shows a simplified cross-sectional view of the ankle bandage taken along line 4—4 of FIG. 1.

FIG. 2 shows the ankle bandage B as seen from behind with the opening for the heel 4 and the above located seam 7. At arrows 10', distal tapering portions 30 of the lower ends 20 of supporting body 11 form a heel support 31 which is illustrated in FIGS. 2 and 4 below the instep region of the user's foot. As indicated in FIG. 2, no overlap exists between the tapering portions 30 of the lower ends 20 of the supporting body 11 in this area.

The supporting body 11 is initially made from a flat sheet of heat formable material and is comprised of two essentially parallel rail portions 18 which are coupled on sides of the upper ends by a joining portion 19 to form an inverted U-shape. The lower ends 20 of the rail portions 18 narrow into distal tapering portions which form the heel support 31 after being bent in the direction of arrows 10' in FIG. 2.

Figure 3:
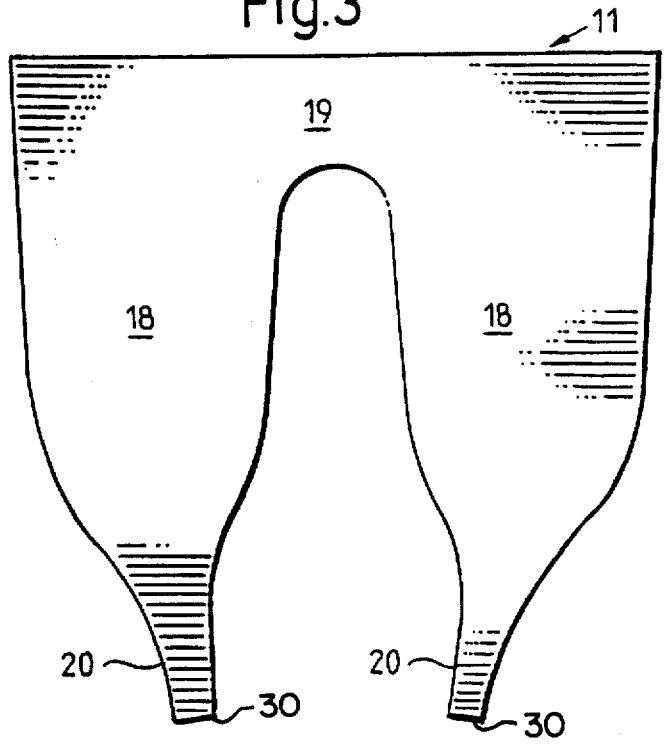
FIG. 3 shows a supporting body for use in a bandage according to FIGS. 1 and 2.

The supporting body 11 does not necessarily have to be designed exactly as in FIG. 3. When supporting body 11 is made of a thermoplastic material, the supporting body 11 is adjusted to a patient after heating to a plastic state (about 40–60° C.); in such a case it is preferred that the support body be an integral, one-piece structure such as illustrated in FIG. 3. The supporting body 11 does not have to be symmetrical with respect to the inside and the outside of the foot and the lower ends 20 of the rail portions 18 do not have to be equal in length. However, it is desirable that supporting body 11 be symmetrical, since such a design eliminates the risk of erroneously fitting the supporting body 11 along the wrong side of the leg and ankle by reversing the rail portions 18.

Figure 5:
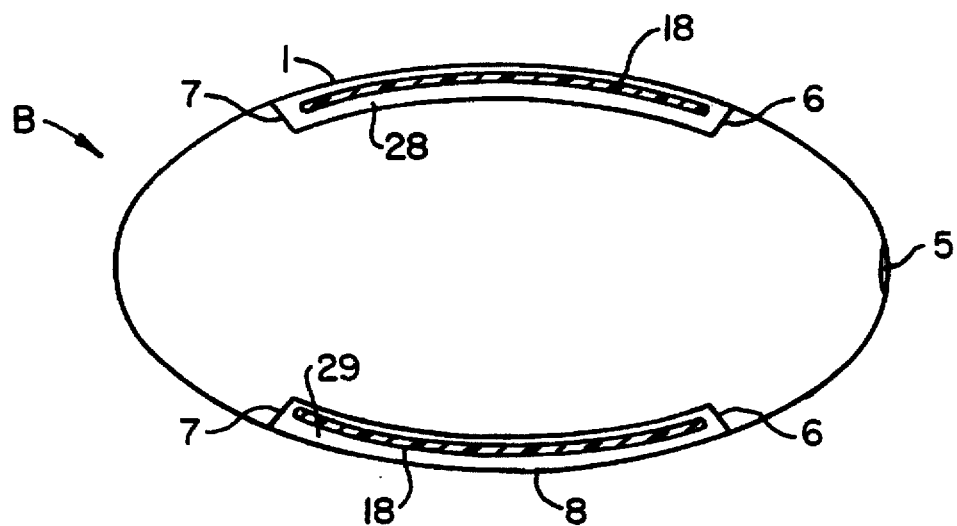
FIG. 5 shows a simplified cross-sectional view of the ankle bandage taken along line 5—5 of FIG. 1.

When adjusting an ankle bandage according to the invention onto a patient, the following steps are followed. A supporting body, e.g. as 11 in FIG. 3, is inserted into a correspondingly shaped pocket 25 in the main body 1 of the ankle bandage, i.e. in main body portions 8, 9, 10 according to FIGS. 1 and 2. (See also FIGS. 4 and 5). The bandage is then heated, either by dipping it into heated water or heating the bandage in a microwave oven if the material of the supporting body 11 is of a type that is capable of absorbing micro waves, in order to bring the supporting body 11 to a temperature corresponding to a plastic state. The ankle bandage is applied from the back of the leg and below the foot of a patient and then tightened by fasteners on the front of the bandage. At least one stabilizing band may be applied, so that accurate adjustment of the bandage is achieved with respect to the shape of the ankle area of the particular patient. By having the inside material layer 27 defining the pocket 25 on the inside of the bandage being made from a heat insulating material, there is no risk of discomfort or injury due to the possibility of relatively high temperatures of the supporting body. The presence of insulating material on the inside of the bandage as well as the outside also contributes to maintaining the supporting body 11 in a plastic state for a sufficiently long period of time to ensure excellent adjustment of the ankle bandage.

While the invention has been described with respect to its preferred embodiments, other alternative modifications can be used, which fall within the scope of the claims. For example, other materials may be used for the supporting body 11 beside thermoplastic materials, such as a plastic material which cures in another way to fit on the user's ankle. The supporting body 11 may also consist of initially separate rail portions 18, which are fixed relative to each other in connection with or after adjustment of the bandage onto the patient.

The dimensions of the bandage and particularly of the supporting body 11 are chosen to ensure adequate fixation in the ankle area, but as is mentioned above, the design of the supporting body may be varied as long as the function of providing an ankle support, a joining portion and a heel support is obtained that does not limit the pivoting motion of the ankle.

In one embodiment, the bandage comprises a heel opening, which defines a lower edge of the pocket 25 containing the supporting body 11. Alternatively, the heel opening may be smaller or possibly eliminated. If no heel opening is used, then the pocket is limited by a continuation of the seam 7, which may have an extension following the outline of the lower part of the edge 4 in FIG. 1.

In order to allow transmission of body moisture, the supporting body 11 is preferably perforated with a number of holes.

A suitable material for the main body 1 is neoprene rubber having laminated layers of nylon jersey on the surfaces.

What is claimed is:

1. An ankle bandage comprising:
   a main body, sized to receive a user's foot, having an upper periphery sized to surround a user's leg and an instep region sized to extend beneath the user's foot;
   the instep region comprising a central portion situated beneath the user's foot;
   said main body having an inside surface, said inside surface comprising a medial side surface, a lateral side surface, a posterior side surface and an anterior side surface;
   a one-piece, stabilizing support body comprising medial and lateral rails, having upper and lower ends, and a joining portion coupling the upper ends;

said medial and lateral rails lying adjacent the medial and lateral side surfaces with said lower ends positioned at said central portion of said instep region; and said upper and lower ends of said medial and lateral rails having widths, said widths of said lower ends being substantially less than said widths of said upper ends so as to allow a relatively unimpeded walking motion while avoiding abrasive injury to the foot.

2. The ankle bandage according to claim 1, wherein the main body is made from a flexible, resilient, heat insulating material.

3. The ankle bandage according to claim 2, wherein the heat insulating material is neoprene.

4. The ankle bandage according to claim 1, wherein the main body further comprises a front closure, which may be opened to facilitate adjusting the ankle bandage onto the user's leg and foot.

5. The ankle bandage according to claim 1, wherein the main body has an opening sized to receive a user's heel.

6. The ankle bandage according to claim 1, wherein a pocket is defined between the inside surface of the main body along the medial side surface, the lateral side surface and the posterior side surface and an inside material layer.

7. The ankle bandage according to claim 6, wherein the inside material layer is a flexible, resilient, heat insulating material.

8. The ankle bandage according to claim 1, wherein the stabilizing support body is perforated to allow air and moisture to pass through from the user's leg and foot to an outside surface of the main body.

9. The ankle bandage according to claim 1, wherein the stabilizing support body is an initially flat, sheet of material, so that the stabilizing support body can be custom molded to a user's leg and foot.

10. The ankle bandage according to claim 1, wherein the stabilizing support body is made from a material which can absorb microwaves to achieve a formable plastic state.

11. The ankle bandage according to claim 10, wherein the material for the stabilizing support body is a thermoplastic which is heat formable at a temperature above the body temperature and cools to a rigid, non-plastic state.

12. The ankle bandage according to claim 1, wherein the joining portion is positioned adjacent to the posterior side surface of the main body.

13. The ankle bandage according to claim 1, wherein the upper widths of the rails are sized to enclose a user's ankle.

14. The ankle bandage according to claim 1, wherein distal tapering portions of the lower ends of the medial and lateral rails are bent inwards toward the instep region to form a heel support.

15. The ankle bandage according to claim 14, wherein the distal tapering portions are positioned adjacent to each other and do not overlap in the instep region.

16. The ankle bandage according to claim 1, wherein a stabilizing band is helically wrapped around the main body and instep region to provide additional support and adjustability.

17. An ankle bandage comprising:

a main body, sized to receive a user's foot, having an upper periphery sized to surround a user's leg and an instep region sized to extend beneath the user's foot;

the instep region comprising a central portion situated beneath the user's foot;

said main body having an inside surface, said inside surface comprising a medial side surface, a lateral side surface, a posterior side surface and an anterior side surface;

said main body being made from a flexible, resilient, heat insulating material;

a one-piece, stabilizing support body comprising medial and lateral rails, having upper and lower ends, and a joining portion coupling the upper ends;

said support body being made from a flat sheet of material which is heat formable at a temperature above the body temperature and rigid when cooled;

said medial and lateral rails lying adjacent the medial and lateral side surfaces with said lower ends positioned at said central portion of said instep region; and said upper and lower ends of said medial and lateral rails having widths, said widths of said lower ends being substantially less than said widths of said upper ends so as to allow a relatively unimpeded walking motion while avoiding abrasive injury to the foot.

18. An ankle bandage comprising:

a main body, sized to receive a user's foot, having an upper periphery sized to surround a user's leg and an instep region sized to extend beneath the user's foot;

the instep region comprising a central portion situated beneath the user's foot;

said main body having an inside surface, said inside surface comprising a medial side surface, a lateral side surface, a posterior side surface and an anterior side surface;

a one-piece, stabilizing support body comprising medial and lateral rails, having upper and lower ends, and a joining portion coupling said me upper ends;

said medial and lateral rails lying adjacent the medial and lateral side surfaces with said lower ends positioned such that the lower ends do not overlap to form a heel support at said central portion of said instep region; and said upper and lower ends of said medial and lateral rails having widths, said widths of said lower ends being substantially less than said widths of said upper ends so as to allow a relatively unimpeded walking motion while avoiding abrasive injury to the foot.

* * * * *